US00PP22026P2

(12) United States Plant Patent
Herrera Valenzuela et al.

(10) Patent No.: US PP22,026 P2
(45) Date of Patent: Jul. 12, 2011

(54) ***ALSTROEMERIA* PLANT NAMED 'JAOFI'**

(50) Latin Name: *Alstroemeria hybrida*
Varietal Denomination: Jaofi

(75) Inventors: Camilo Herrera Valenzuela, Bogotá (CO); Henry Belalcázar Valencia, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 0 days.

(21) Appl. No.: 12/660,104

(22) Filed: Feb. 19, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu
(74) *Attorney, Agent, or Firm* — C. A. Whealy

(57) ABSTRACT

A new and distinct cultivar of *Alstroemeria* plant named 'Jaofi', characterized by its erect and strong flowering stems; vigorous growth habit; large dark purple and white-colored flowers with greyed purple-colored flecks and streaks, flowers arranged in symmetrical umbels; and excellent postproduction longevity.

1 Drawing Sheet

Botanical designation: *Alstroemeria hybrida.*
Cultivar denomination: 'JAOFI'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Jaofi'.

The new *Alstroemeria* plant is a product of a planned breeding program conducted by the Inventors in Madrid, Cundinamarca, Colombia. The objective of the breeding program was to create new *Alstroemeria* cultivars with desirable plant qualities, attractive flower color and excellent postproduction longevity.

The new *Alstroemeria* plant originated from a cross-pollination conducted in January, 2005 by the Inventors in Madrid, Cundinamarca, Colombia of a proprietary selection of *Alstroemeria hybrida* identified as code number JA 953, not patented, as the female, or seed, parent with a proprietary selection of *Alstroemeria hybrida* identified as code number JA 4222, not patented, as the male, or seed, parent. The new *Alstroemeria* plant was discovered and selected by the Inventors as a single flowering plant from within the progeny of the stated cross-pollination grown in a controlled greenhouse environment in Madrid, Cundinamarca, Colombia in March, 2006.

Asexual reproduction of the new *Alstroemeria* plant by rhizome divisions in a controlled greenhouse environment in Madrid, Cundinamarca, Colombia since May, 2006, has shown that the unique features of this new *Alstroemeria* plant are stable and reproduced true to type in successive generations.

SUMMARY OF THE INVENTION

Plants of the new *Alstroemeria* have not been observed under all possible environmental and cultural conditions. The phenotype may vary somewhat with variations in environment and cultural practices such as temperature and light intensity without, however, any variance in genotype.

The following traits have been repeatedly observed and are determined to be the unique characteristics of 'Jaofi'. These characteristics in combination distinguish 'Jaofi' as a new and distinct cultivar of *Alstroemeria* plant:

1. Erect and strong flowering stems.
2. Vigorous growth habit.
3. Large dark purple and white-colored flowers with greyed purple-colored flecks and streaks, flowers arranged in symmetrical umbels.
4. Excellent postproduction longevity.

Plants of the new *Alstroemeria* can be compared to plants of the female parent selection. Plants of the new *Alstroemeria* differ from plants of the female parent selection primarily in flower color as plants of the female parent selection have red purple, yellow and white-colored flowers.

Plants of the new *Alstroemeria* can be compared to plants of the male parent selection. Plants of the new *Alstroemeria* and the male parent selection both have purple and white-colored flowers, however the white-colored areas are more prominent and defined on plants of the male parent selection in comparison to plants of the new *Alstroemeria.*

Plants of the new *Alstroemeria* can be compared to plants of *Alstroemeria hybrida* 'Napoli', not patented. In side-by-side comparisons plants of the new *Alstroemeria* differed primarily from plants of 'Napoli' in the following characteristics:

1. Plants of the new *Alstroemeria* had more flowers per inflorescence than plants of 'Napoli'.
2. Flowers of plants of the new *Alstroemeria* had larger perianth segments than plants of 'Napoli'.
3. Plants of the new *Alstroemeria* and 'Napoli' differed in flower color as plants of 'Napoli' had red purple and pale yellow-colored flowers.
4. Plants of the new *Alstroemeria* had shorter pedicels than plants of 'Napoli'.
5. Plants of the new *Alstroemeria* and 'Napoli' differed in anther and pollen color.
6. Plants of the new *Alstroemeria* and 'Napoli' differed in style and stigma color.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph at the bottom of the sheet comprises a side perspective view of a typical flowering stem of 'Jaofi'.

The photograph at the top of the sheet is a close-up view of a typical inflorescence of 'Jaofi'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, maximum day temperatures averaged 31.5° C., maximum night temperatures averaged 6° C. and light levels averaged 21.4 KWH/m$^2$. Plants used for the photographs and description were two years old. Color references are made to The Royal Horticultural Society Colour Chart, 2007 Edition, except where general terms of ordinary dictionary significance are used.

Botanical classification: *Alstroemeria hybrida* 'Jaofi'.

Parentage:

*Female, or seed, parent.*—Proprietary selection of *Alstroemeria hybrida* identified as code number JA 953, not patented.

*Male, or pollen, parent.*—Proprietary selection of *Alstroemeria hybrida* identified as code number JA 4222, not patented.

Propagation:

*Type.*—By rhizome divisions.

*Time to initiate roots.*—About two weeks at temperatures ranging from about 6° C. to 32° C.

*Time to produce a rooted young plant.*—About eight weeks at temperatures ranging from about 6° C. to 32° C.

*Root description.*—Fleshy, medium in thickness; close to 155A in color.

*Rooting habit.*—Freely branching; dense.

*Rhizomes.*—Shape: Rounded. Length: About 5 cm. Diameter: About 1.06 cm. Texture: Fleshy. Color: Close to NN155B.

Plant description:

*Plant and growth habit.*—Upright; freely branching, bushy appearance; vigorous growth habit.

*Time from planting to harvest of cut flowers.*—About 19 weeks.

Flowering stem description:

*Aspect.*—Erect.

*Length.*—About 110 cm to 125 cm.

*Diameter.*—About 6 mm.

*Internode length.*—About 1.8 cm to 5 cm.

*Strength.*—Strong.

*Texture.*—Smooth, glabrous.

*Color.*—Close to 146D.

Foliage description:

*Arrangement.*—Alternate, simple.

*Length.*—About 11.6 cm.

*Width.*—About 3.2 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper and lower surfaces: Close to 146B. Fully expanded leaves, upper surface: Close to N137A; venation, close to 146A. Fully expanded leaves, lower surface: Close to 137B; venation, close to 146B.

*Petioles.*—Length: About 4.3 cm. Diameter: About 7 mm. Texture, upper and lower surfaces: Smooth, glabrous. Color, upper and lower surfaces: Close to 146C.

Flower description:

*Flower type and arrangement.*—Single cup-shaped flowers arranged in compound umbels; flowers face upright to outwardly; perianth segments separate.

*Flowering habit.*—Freely flowering with about 18 open flowers and flower buds per inflorescence.

*Natural flowering season.*—Flowering continuous year round in a greenhouse in Colombia; plants begin flowering about 19 weeks after planting.

*Fragrance.*—None detected.

*Flower longevity as a cut flower.*—About two weeks; flowers not persistent.

*Flower buds* (*showing color*).—Length: About 4.2 cm. Diameter: About 1.6 cm. Shape: Oblanceolate to obovate. Color: Close to N79C to N79C.

*Umbel height.*—About 13.5 cm.

*Umbel diameter.*—About 12.5 cm by 14 cm.

*Flower diameter.*—About 5.7 cm.

*Flower length* (*height*).—About 5.5 cm.

*Flower depth.*—About 6.5 cm.

*Perianth.*—Arrangement: Six arranged in two whorls, each whorl with two lateral and one median segments. Inner perianth, lateral segments: Length: About 5.9 cm. Width: About 1.8 cm. Shape: Oblanceolate. Apex: Cuspidate. Base: Attenuate. Margin: Entire; towards the apex, slightly sinuate. Texture, upper and lower surfaces: Smooth, glabrous; satiny. Color, when opening, upper surface: Towards the apex, close to N79C; mid-section, close to 157B; towards the base, close to 186D; flecks and streaks, close to 183A. Color, when opening, lower surface: Towards the apex, close to 79C; mid-section, close to N80C to N80D; towards the base, close to N79D. Color, fully opened, upper surface: At the apex, close to N79A; towards the mid-section, close to N79D graduating to N81B to N81C; mid-section, close to 157D; towards the base, close to 84C; flecks and streaks, close to 183A. Color, fully opened, lower surface: Towards the apex, close to N79B to N79C; mid-section, close to 155A; towards the base, close to N80C to N80D. Inner perianth, median segment: Length: About 4.5 cm. Width: About 1.8 cm. Shape: Oblanceolate. Apex: Cuspidate. Base: Attenuate. Margin: Entire; towards the apex, slightly sinuate. Texture, upper and lower surfaces: Smooth, glabrous; satiny. Color, when opening, upper surface: Close to N79C; towards the base, close to 186D. Color, when opening, lower surface: Close to N79C to N79D. Color, fully opened, upper surface: At the apex, close to N79B; towards the mid-section, close to 79B to 79C; towards the base, close to N81C to N81D; flecks and streaks, close to 183A. Color, fully opened, lower surface: Towards the apex, close to 83A to 83B; mid-section and base, close to N81D. Outer perianth, lateral segments: Length: About 5.4 cm. Width: About 3 cm. Shape: Obovate. Apex: Rounded and slightly mucronate. Base: Attenuate. Margin: Entire. Texture, upper and lower surfaces: Smooth, glabrous; satiny. Color, when opening, upper surface: Towards the apex, close to N79B; mid-section, close to N79C; towards the base, close to 145D. Color, when opening, lower surface: At the apex, close to 146B; towards the mid-section, close to N79B; mid-section and base, close to N79C to N79D. Color, fully opened, upper surface: Apex and towards the mid-section, close to N79A; mid-section, close to N79B; towards the base, close to N81C to N81D. Color, fully opened, lower surface: Apex and towards the mid-section, close to 79A; mid-section and base, close to N79B to N79C. Outer perianth, median segment: Length: About 5.5 cm. Width: About 3.2 cm. Shape: Obovate. Apex: Rounded and slightly mucronate. Base: Attenuate. Margin: Entire. Texture, upper and lower surfaces: Smooth, glabrous; satiny. Color, when opening, upper surface: Towards the apex, close to N79B; mid-section, close to N79C; towards the base, close to 145D. Color, when opening, lower surface: At the apex, close to 146B; towards the mid-section, close to N79B; mid-section and base, close to N79C to N79D. Color, fully opened, upper surface: Towards the apex, close to N79A; mid-section, close to N79B to N79C; towards the base, close to N81C to N81D. Color, fully opened, lower surface: Towards the apex, close to N79A; mid-section, close to N81A to N81B; base, close to N81D.

*Pedicels.*—Length: About 2.6 cm. Diameter: About 2.5 mm. Strength: Strong. Angle: About 15° to 25° from the peduncle axis. Texture: Smooth, glabrous. Color: Close to 146C.

*Reproductive organs.*—Stamens: Quantity per flower: Six. Anther shape: Elongated. Anther length: About 7 mm. Anther diameter: About 2.5 mm. Anther color: Close to 187A. Pollen amount: Moderate. Pollen color: Close to 189A. Pistils: Quantity per flower: One. Pistil length: About 5.2 cm. Style length: About 4 cm. Style color: Close to N81D. Stigma shape: Three-parted. Stigma color: Close to N81C. Ovary color: Close to 146B tinted with close to 187B.

*Fruit/seed.*—Fruit and seed development has not been observed.

Disease/pest resistance: Plants of the new *Alstroemeria* have not been observed to be resistant to pathogens and pests common to *Alstroemeria*.

It is claimed:

1. A new and distinct *Alstroemeria* plant named 'Jaofi' as illustrated and described.

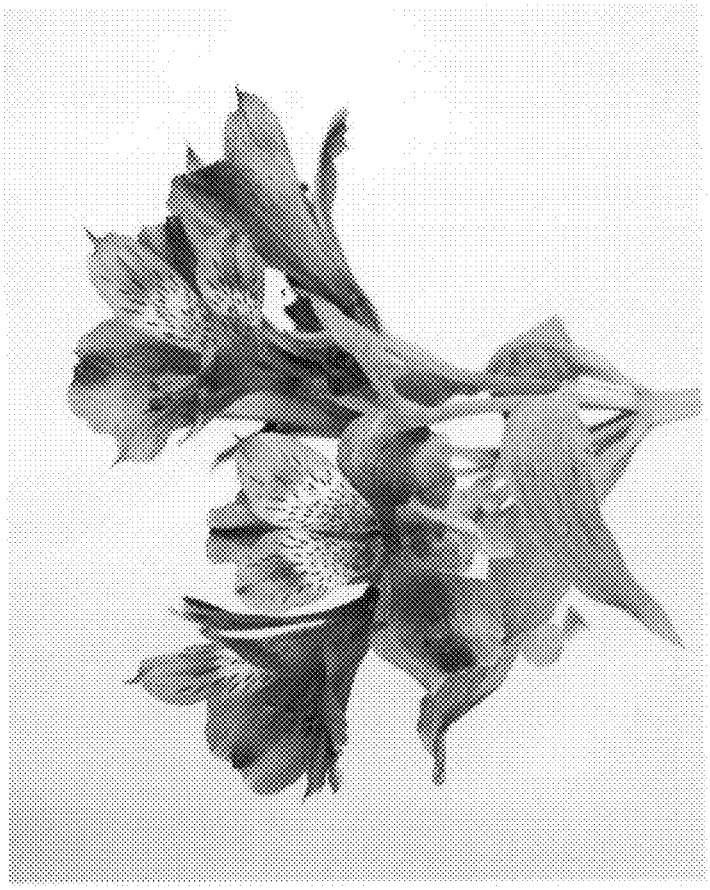
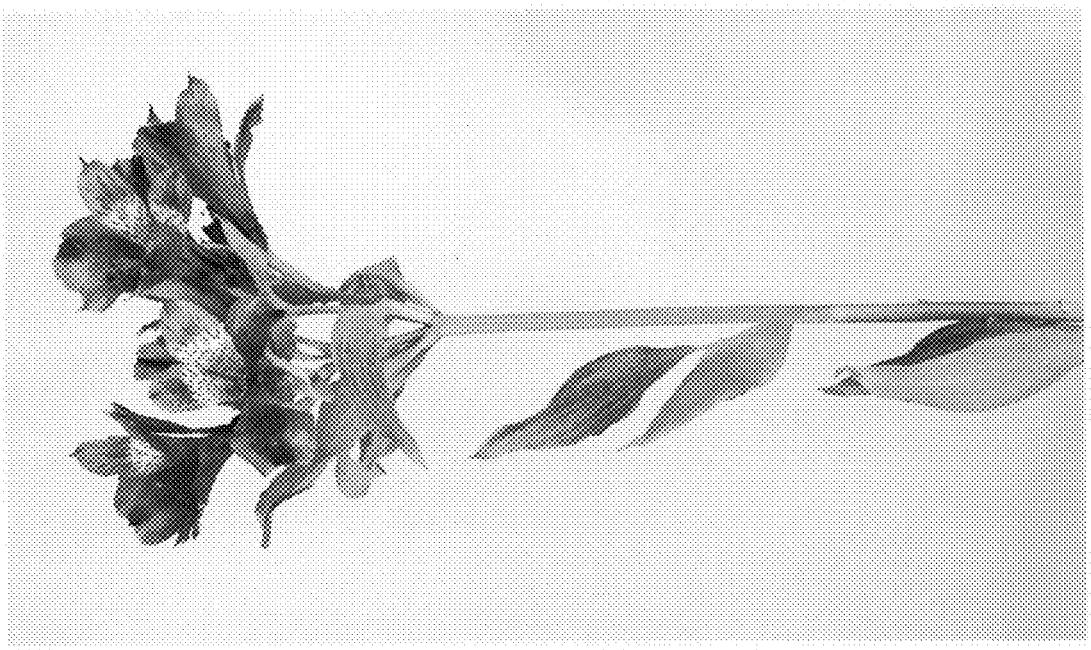

* * * * *